(12) United States Patent (10) Patent No.: US 10,278,853 B2
Sutti et al. (45) Date of Patent: May 7, 2019

(54) LIMITING DYNAMIC CORD FOR AN ORTHOSIS OR PROSTHESIS OR WALKER

(71) Applicants: Nathan Joseph Sutti, Plano, TX (US); Franck Vautrin, Dallas, TX (US)

(72) Inventors: Nathan Joseph Sutti, Plano, TX (US); Franck Vautrin, Dallas, TX (US)

(73) Assignee: Kinematic Improvements LLC, Plano, TX (US)

( * ) Notice: Subject to any disclaimer, the term of this patent is extended or adjusted under 35 U.S.C. 154(b) by 667 days.

(21) Appl. No.: 14/859,107

(22) Filed: Sep. 18, 2015

(65) Prior Publication Data

US 2016/0278960 A1    Sep. 29, 2016

Related U.S. Application Data

(60) Provisional application No. 62/138,535, filed on Mar. 26, 2015.

(51) Int. Cl.
| | |
|---|---|
| *A61F 5/00* | (2006.01) |
| *A61F 5/01* | (2006.01) |
| *A61H 3/00* | (2006.01) |
| *A61H 1/02* | (2006.01) |
| *A61H 3/04* | (2006.01) |

(52) U.S. Cl.
CPC .......... *A61F 5/0111* (2013.01); *A61F 5/0127* (2013.01); *A61H 3/00* (2013.01); *A61F 2005/0137* (2013.01); *A61F 2005/0165* (2013.01); *A61F 2005/0179* (2013.01); *A61F 2005/0197* (2013.01); *A61H 1/0266* (2013.01); *A61H 3/04* (2013.01); *A61H 2003/007* (2013.01); *A61H 2201/0119* (2013.01); *A61H 2201/164* (2013.01); *A61H 2201/165* (2013.01); *A61H 2201/1635* (2013.01)

(58) Field of Classification Search
CPC ................. A61F 2005/0197; A61F 2005/0165
USPC .................................. 602/27, 28, 3; D8/384
See application file for complete search history.

(56) References Cited

U.S. PATENT DOCUMENTS

| | | | | |
|---|---|---|---|---|
| 3,316,900 | A * | 5/1967 | Young | A61F 5/0125 602/16 |
| D381,893 | S * | 8/1997 | Klamm | D2/891 |
| 5,817,038 | A * | 10/1998 | Orange | A61F 13/041 602/3 |
| 9,199,571 | B2 * | 12/2015 | Leung | B60P 7/0823 |
| 9,326,880 | B2 * | 5/2016 | Szczepanski | A61F 5/0127 |
| 2015/0045709 | A1 * | 2/2015 | Wiley | A61F 5/0111 602/28 |

(Continued)

FOREIGN PATENT DOCUMENTS

WO    WO 02065942 A2 *  8/2002  ............ A61F 5/0111

*Primary Examiner* — Kim M Lewis
(74) *Attorney, Agent, or Firm* — Mohr Intellectual Property Law Solutions, P.C.

(57) ABSTRACT

A movement limiting system for supporting, aligning, preventing, or correcting deformities includes a calf shell that is adapted to form around a calf of a human user. A heel shell is adapted to form around a heel of the human user. A calf shell flap is connected to a calf shell ring. A heel shell flap is connected to a heel shell ring. A cord has a first end and a second end. The first end is connected to the calf shell ring and the second end is connected to the heel shell ring. Additionally, the cord can be connected to a user's leg at one end and a walker at the other end.

17 Claims, 7 Drawing Sheets

(56) References Cited

U.S. PATENT DOCUMENTS

2015/0182775 A1\* 7/2015 Toback ............... A63B 5/16
    482/130

\* cited by examiner

LIMITING DYNAMIC CORD FOR AN ORTHOSIS OR PROSTHESIS OR WALKER

RELATED APPLICATION

This application claims priority to provisional patent application U.S. Ser. No. 62/138,535 filed on Mar. 26, 2015, the entire contents of which is herein incorporated by reference.

BACKGROUND

The embodiments herein relate generally to medical equipment and an orthosis and/or prosthesis.

Prior to embodiments of the disclosed invention, an individual with any pathology that created a problem to normal gait kinematics may have an inability to control tibial progression, control hyperextension and/or have the inability to push off their forefoot in late stance for proper propulsion. Furthermore, complications to gait kinematics can also include uncontrolled femoral rotation, uncontrolled genu valgum, undue knee flexion and dorsiflexion. Embodiments of the disclosed invention can be used for supporting, aligning, preventing, or correcting deformities such as this.

SUMMARY

A movement limiting system for supporting, aligning, preventing, or correcting deformities includes a calf shell that is adapted to form around a calf of a human user. A heel shell is adapted to form around a heel of the human user. A calf shell flap is connected to a calf shell ring. A heel shell flap is connected to a heel shell ring. A cord has a first end and a second end. The first end is connected to the calf shell ring and the second end is connected to the heel shell ring.

In some embodiments, a first end clip can fuse the cord to itself proximate to the calf shell ring. A second end clip can fuse the cord to itself proximate the heel shell ring. A sheath can cover the cord, being longer than the cord, such that the sheath is wrapped around the calf shell ring and the heel shell ring with the cord. A first end sheath and a second end sheath covering a portion of the sheath. The first end can be a calf ball and the second end can be a heel ball.

A movement limiting system can be used for supporting, aligning, preventing, or correcting deformities. The movement limiting system includes a walker further comprising a first structural member attached to a first wheel and a second structural member attached to a second wheel. A first structural member connection assembly can be connected to the first structural member and adapted to wrap around a first leg of a human user. A second structural member connection assembly can be connected to the second structural member and adapted to wrap around a second leg of the human user.

In some embodiments, a first ring can be attached to at least one cuff. A carabiner can be attached to the first ring. A second ring can be inserted around the second structural member. A cord can be connected to the carabiner and the first ring. A first end clip can fuse the cord around the carabiner. A second end clip can fuse the cord around the second ring. A sheath can cover the cord, the first end clip and the second end clip.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

Figure 1:
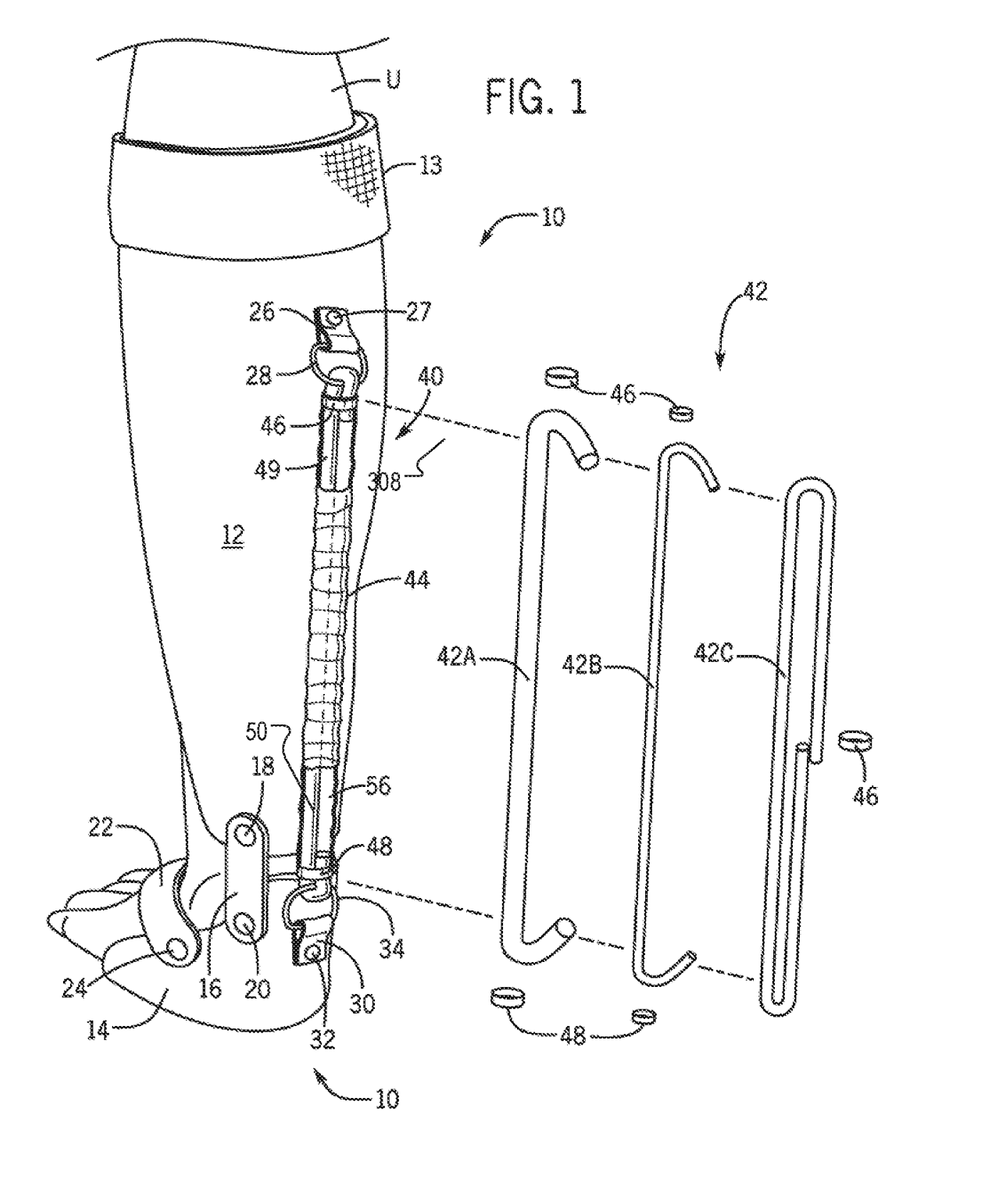
FIG. 1 is an exploded rear perspective view of an embodiment of the invention in use.

By way of example, and referring to FIG. 1, one embodiment of the movement limiting system 10 comprises calf shell 12 connected to heel shell 14. Calf shell 12 is adapted to fit around the curvature of a calf of user U and can be connected to a calf of user U with calf band 13. Likewise, heel shell 14 is adapted to fit around the curvature of a heel of user U. Calf shell 12 is rotatably coupled to first connecting member 16 with first calf shell connecting member fastener 18. Heel shell 14 is rotatably coupled to first connecting member 16 with first heel shell connecting member fastener 20. Heel shell 14 is further mechanically coupled to foot strap 22 with first foot strap fastener 24.

Calf shell 12 is operably connected to calf shell flap 26 with calf shell flap connector 27. Calf shell flap 26 is operable connected to calf shell ring 28. Similarly, heel shell 14 is operably connected to heel shell flap 30 with heel shell flap connector 32. Heel shell flap 30 is operable connected to heel shell ring 34.

Calf shell ring 28 is connected to heel shell ring 34 with dynamic cord assembly 40. Dynamic cord assembly 40 comprises cord 42. There are many kinds of cord 42 that could work and can rage in different thicknesses. Cord 42A is a thick cord. As used in this application a thick cord has a diameter greater than 5 millimeters. Cord 42B is thin cord. As used in this application, a thin cord is a cord that has a diameter less than or equal to 5 millimeters. Cord 42C is a cut band, this is a cord made from a band that is cut but otherwise is longer than the thick cord or the thin cord and shows a double cord set up. The double cord in any embodiment can be one solid single loop or cut with assembly clip. When a single solid loop is used the ring is split for assembly and then fused back into its original shape. Collectively, any of the set consisting of the thick cord, the thin cord and the cut band is referred two by the genus cord 42.

Cord 42 is covered by sheath 44 such that sheath 44 is longer than cord 42. A first end of cord 42 and sheath 44 are then slid over and around calf shell ring 28 and sealed around calf shell ring 28 with first end clip 46. After that, first end sheath 49 is stretched over calf shell ring 28 and over first end of cord 42 and sheath 44. Following that, second end of cord 42 and sheath 44 are then slid over and around heel shell ring 34 and sealed around heel shell ring 34 with second end clip 48. After that, second end sheath 50 is stretched around heel shell ring 34 and over the second end of cord 42 and sheath 44.

Once dynamic cord assembly 40 is assembled, calf shell flap 26 is operable connected to calf shell ring 28. Then, heel shell flap 30 is operable connected to heel shell ring 34.

Figures 2, 3:
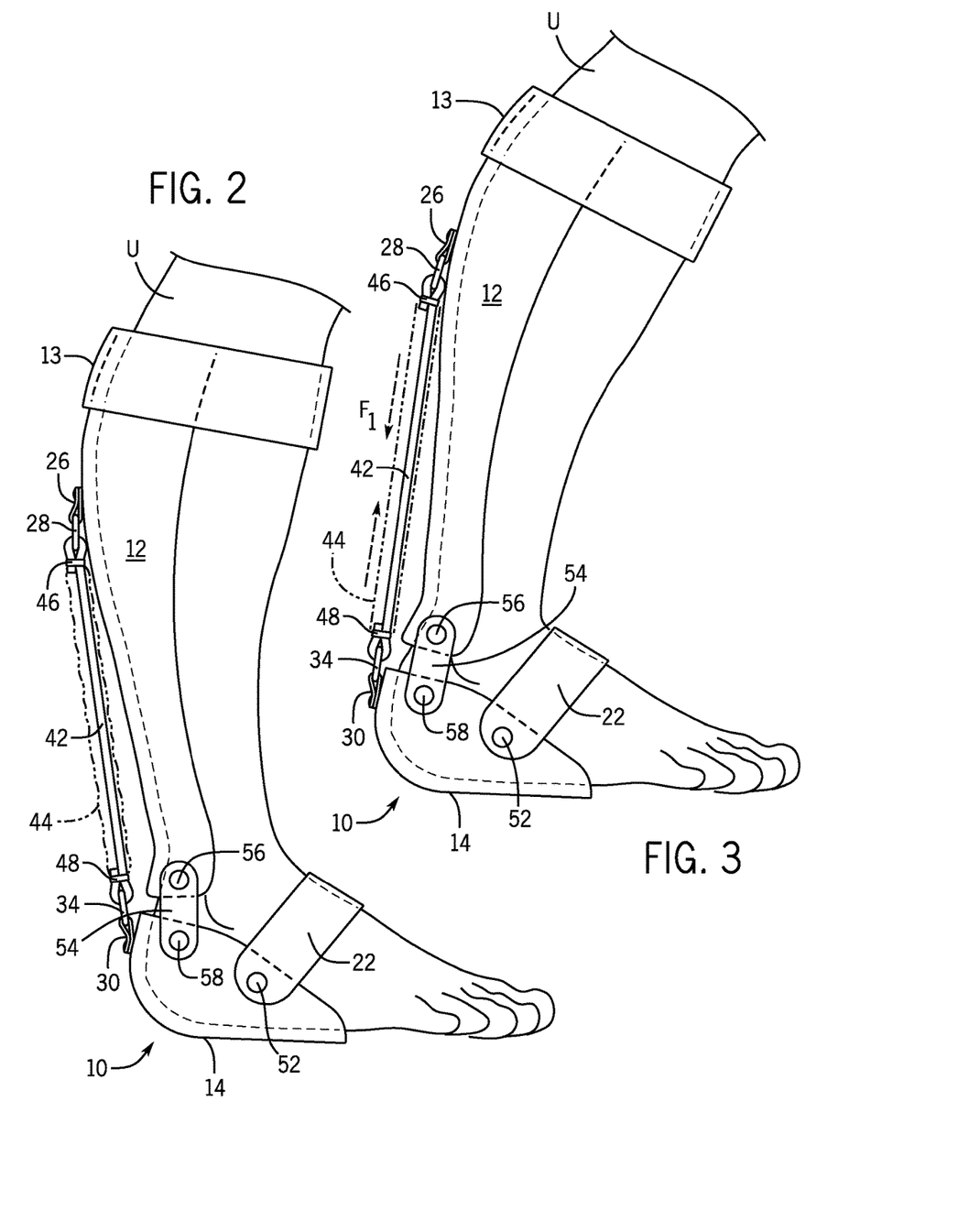
FIG. 2 is side elevation view of an embodiment of the invention shown in a first position.
FIG. 3 is a side elevation view of an embodiment of the invention shown in a second position.

Turning to FIG. 2 and FIG. 3, heel shell 14 is rotatably coupled to foot strap 22 with second foot strap fastener 52. Calf shell 12 is rotatably coupled to second connecting member 54 with second calf shell connecting member fastener 56. Heel shell 14 is rotatably coupled to second connecting member 54 with second heel shell connecting member fastener 58.

Figures 4, 5, 6, 7:
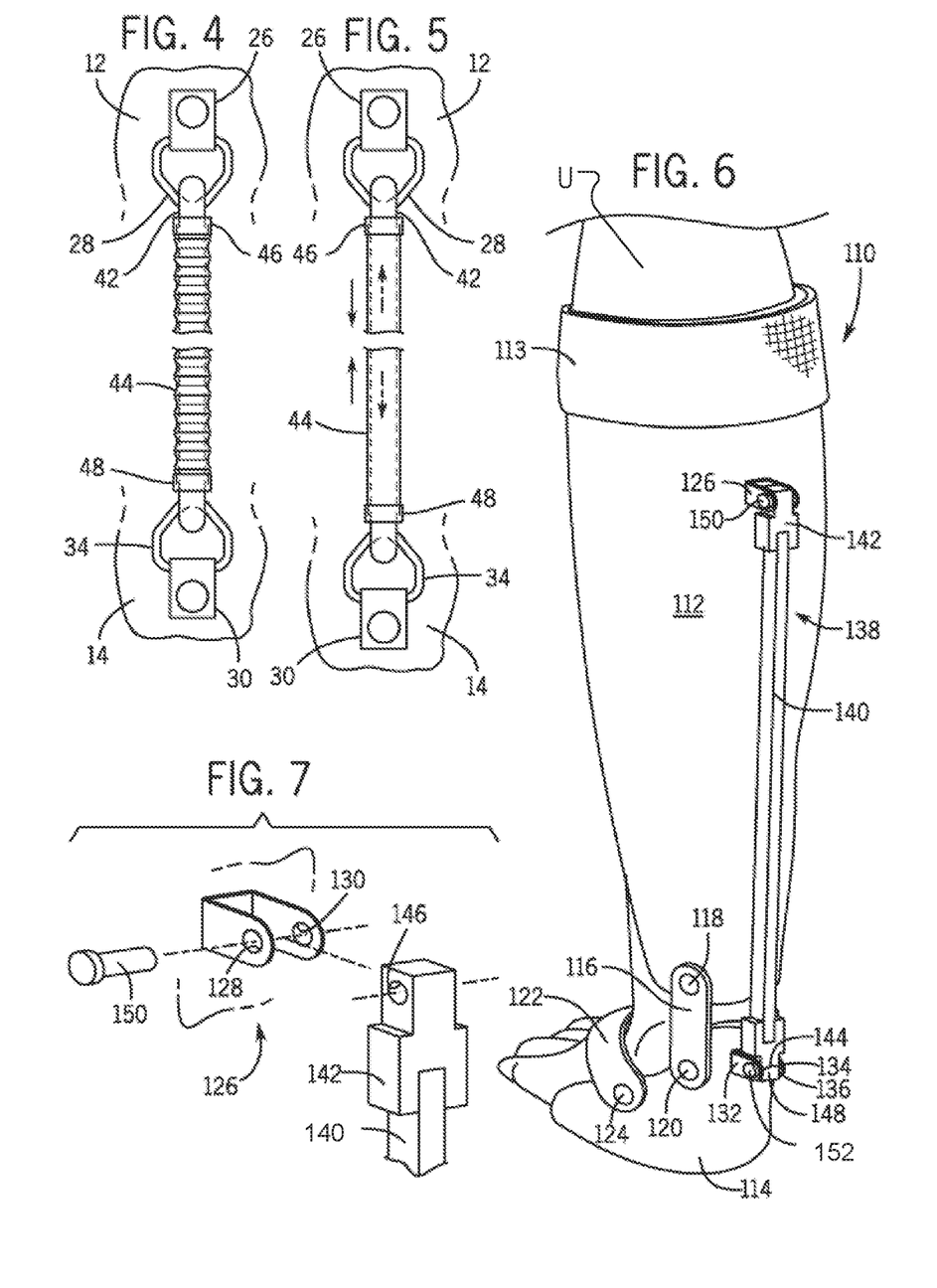
FIG. 4 is a detail rear elevation view showing an embodiment of the invention in a relaxed state.
FIG. 5 is a detail rear elevation view showing an embodiment of the invention in an extended state.
FIG. 6 is a rear perspective view of an embodiment of the invention.
FIG. 7 is a detail exploded perspective view of an embodiment of the invention.

In use, cord 42 cannot extend beyond the length of sheath 44 without a loading failure, i.e. tearing, of cord 42. This exerts a substantial compression force F1 pulling calf shell flap 26 toward heel shell flap 30 and thus cord 42 limits the dynamic motion of user U. FIG. 4 and FIG. 5 show another view of the same motion where sheath 44 appears ruffled when at rest and smooth when under tension.

In FIG. 6 and FIG. 7, one embodiment of the movement limiting system 110 comprises calf shell 112 connected to heel shell 114. Calf shell 112 can be connected to a calf of user U with calf band 113. Calf shell 112 is rotatably coupled to first connecting member 116 with first calf shell connecting member fastener 118. Heel shell 114 is rotatably coupled to first connecting member 116 with first heel shell connecting member fastener 120. Heel shell 114 is further mechanically coupled to foot strap 122 with first foot strap fastener 124.

Calf shell 112 is operably connected to calf shell clevis 126. Calf shell clevis 126 further comprises calf shell clevis first opening 128 and calf shell clevis second opening 130. Similarly, heel shell 114 is operably connected to heel shell clevis 132. Heel shell clevis 132 further comprises heel shell clevis first opening 134 and heel shell clevis second opening 136.

Cord assembly 138 comprises cord 140 chemically fused to calf cord connector 142 at a first end and chemically fused to heel cord connector 144 at a second end. Calf cord connector 142 further comprises calf cord connector opening 146. Similarly, heel cord connector 144 further comprises heel cord connector opening 148. To install cord assembly 138, one inserts calf connector pin 150 through calf shell clevis first opening 128, calf cord connector opening 146 and calf shell clevis second opening 130. Then one inserts heel connector pin 152 through heel shell clevis first opening 134, heel cord connector opening 148 and heel shell clevis second opening 136.

Figure 8:
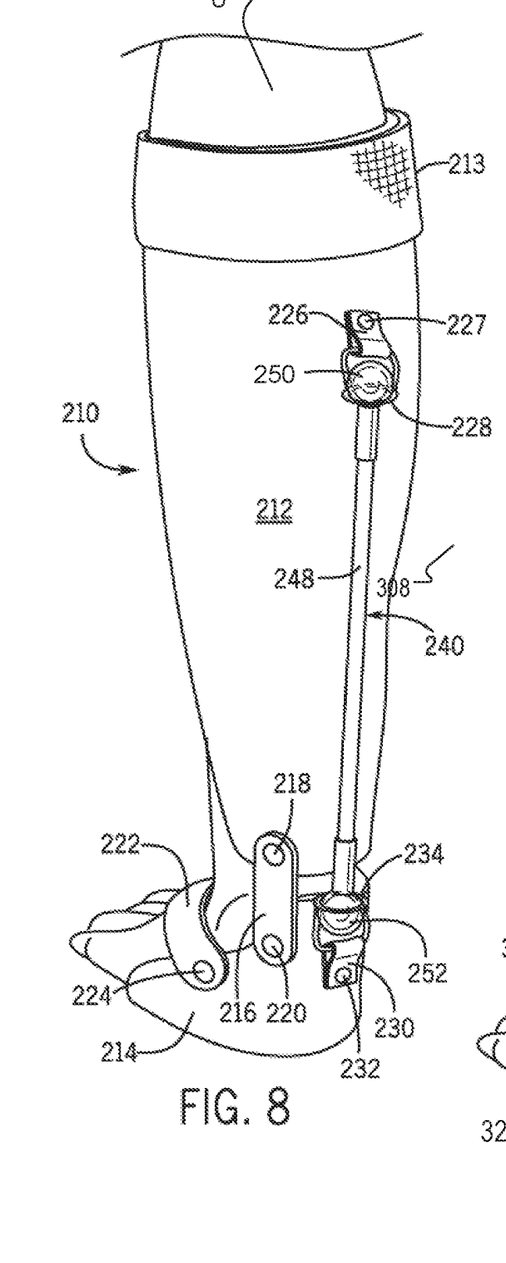
FIG. 8 is a rear perspective view of an embodiment of the invention.

Turning to FIG. 8, one embodiment of the movement limiting system 210 comprises calf shell 212 connected to heel shell 214. Calf shell 212 can be connected to a calf of user U with calf band 213. Calf shell 212 is rotatably coupled to first connecting member 216 with first calf shell connecting member fastener 218. Heel shell 214 is rotatably coupled to first connecting member 216 with first heel shell connecting member fastener 220. Heel shell 214 is further mechanically coupled to foot strap 222 with first foot strap fastener 224.

Calf shell 212 is operably connected to calf shell flap 226 with calf shell flap connector 227. Calf shell flap 226 is operable connected to calf shell ring assembly 228. Calf shell ring assembly 228 further comprises two rings perpendicular to one another. Heel shell 214 is operably connected to heel shell flap 230 with heel shell flap connector 232. Heel shell flap 230 is operable connected to heel shell ring assembly 234. Heel shell ring assembly 234 further comprises two rings perpendicular to one another.

Cord assembly 240 further comprises cord 248 fused to calf ball 250 and heel ball 252. Calf ball 250 is partially housed in calf shell ring assembly 228. Heel ball 252 is partially housed in heel shell ring assembly 234. As noted above, there can be folds, cloth and rings that assist in the connection as well and limiting/assisting motion.

Figure 9:
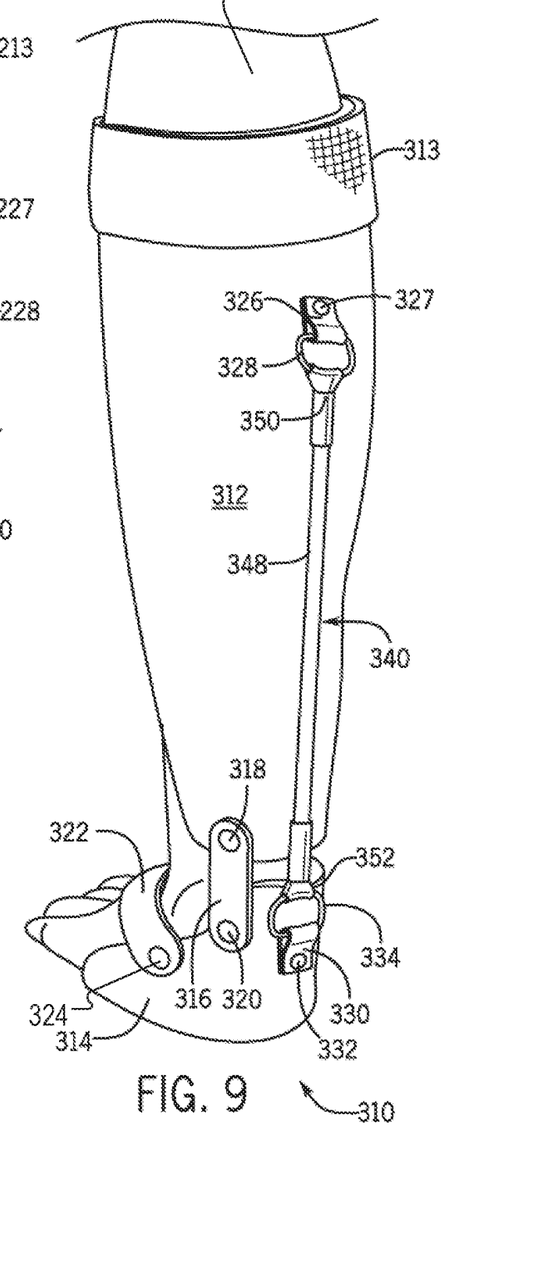
FIG. 9 is rear perspective view of an embodiment of the invention.

Turning to FIG. 9, one embodiment of the movement limiting system 310 comprises calf shell 312 connected to heel shell 314. Calf shell 312 can be connected to a calf of user U with calf band 313. Calf shell 312 is rotatably coupled to first connecting member 316 with first calf shell connecting member fastener 318. Heel shell 314 is rotatably coupled to first connecting member 316 with first heel shell connecting member fastener 320. Heel shell 314 is further mechanically coupled to foot strap 322 with first foot strap fastener 324.

Calf shell 312 is operably connected to calf shell flap 326 with calf shell flap connector 327. Calf shell flap 326 is operable connected to calf shell ring 328. Heel shell 314 is operably connected to heel shell flap 330 with heel shell flap connector 332. Heel shell flap 330 is operable connected to heel shell ring 334.

Cord assembly 340 further comprises cord 348. Cord 348 is attached to calf shell ring 328 with calf shell ring sheath 350. Cord 348 is further attached to heel shell ring 334 with heel shell ring sheath 352. As noted above, there can be folds, cloth and rings that assist in the connection as well and limiting/assisting motion.

Figure 10:
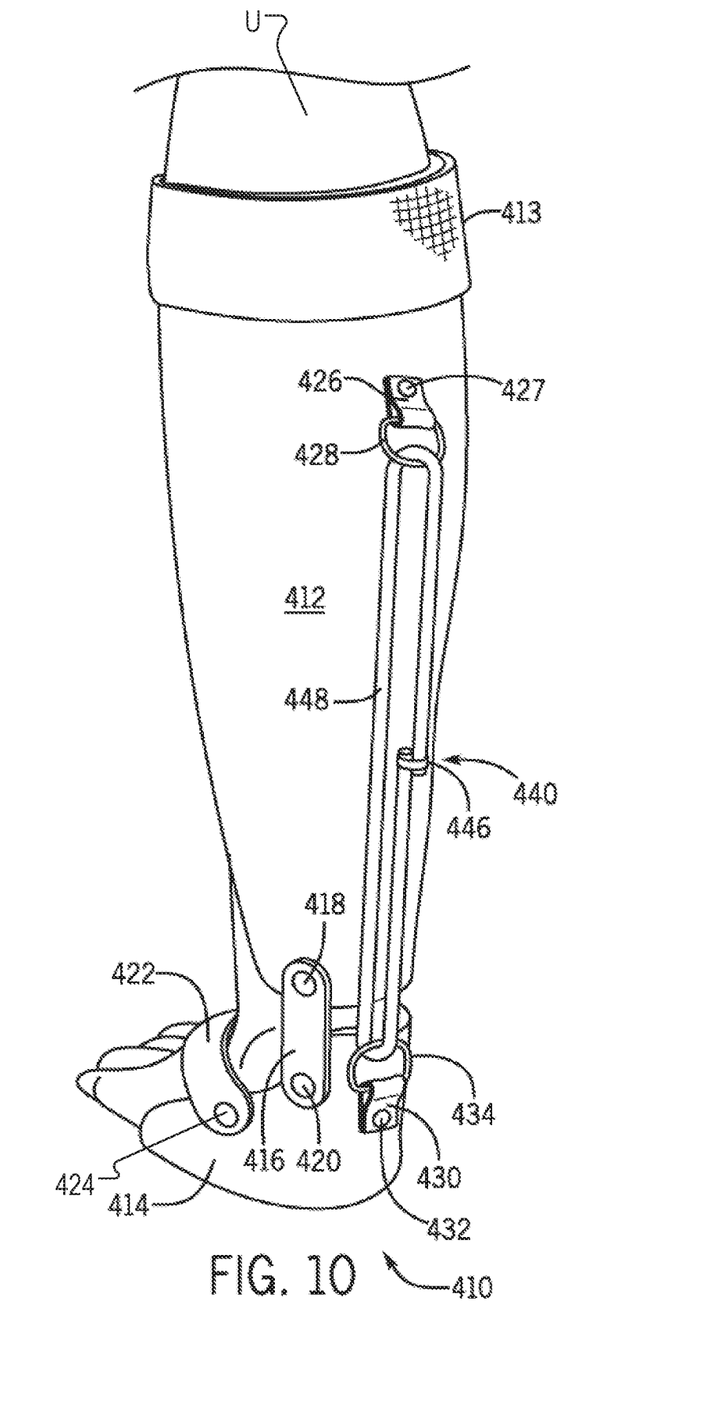
FIG. 10 is a rear perspective view of an embodiment of the invention.

Turning to FIG. 10, one embodiment of the movement limiting system 410 comprises calf shell 412 connected to heel shell 414. Calf shell 412 can be connected to a calf of user U with calf band 413. Calf shell 412 is rotatably coupled to first connecting member 416 with first calf shell connecting member fastener 418. Heel shell 414 is rotatably coupled to first connecting member 416 with first heel shell connecting member fastener 420. Heel shell 414 is further mechanically coupled to foot strap 422 with first foot strap fastener 424.

Calf shell 412 is operably connected to calf shell flap 426 with calf shell flap connector 427. Calf shell flap 426 is operable connected to calf shell ring 428. Heel shell 414 is operably connected to heel shell flap 430 with heel shell flap connector 432. Heel shell flap 430 is operable connected to heel shell ring 434.

Cord assembly 440 comprises cut band 448 wrapped around calf shell ring 428 and heel shell ring 434. Cut band 448 is then attached to itself with first end clip 446. There is no need for an additional end clip (as in other embodiments) due to the length of cut band 448. Cut band 448 is approximately twice the distance from calf shell ring 428 to heel shell ring 434. Cut band 448 can be covered with cloth or rubber as in previous embodiments. As noted above any double cord embodiment can be a single solid loop or cut with an assembly clip. When a solid loop is used the ring split open to connect the cord and fused back into original shape.

Figures 11, 12:
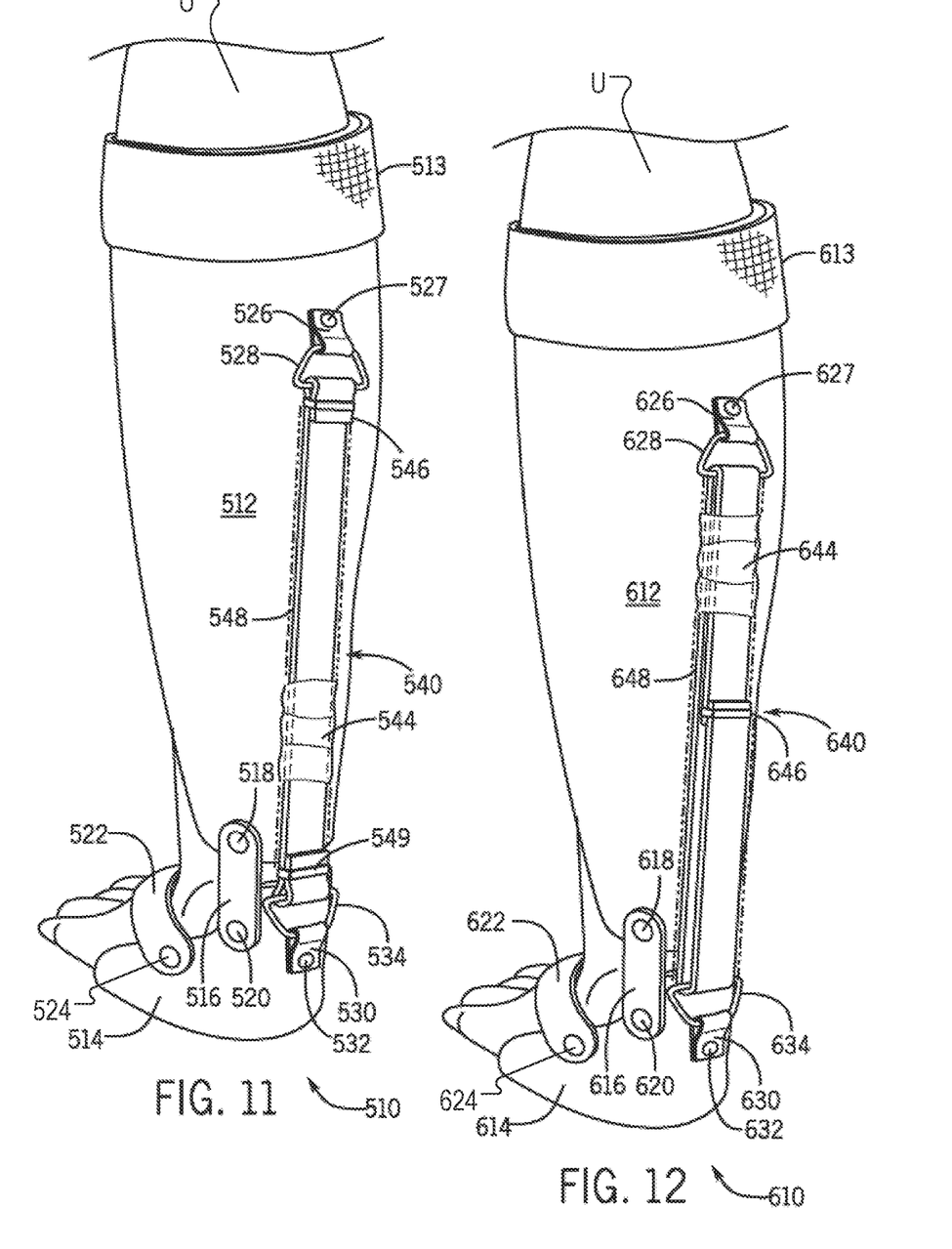
FIG. 11 is rear perspective view of an embodiment of the invention.
FIG. 12 is a rear perspective view of an embodiment of the invention

Turning to FIG. 11, one embodiment of the movement limiting system 510 comprises calf shell 512 connected to heel shell 514. Calf shell 512 can be connected to a calf of user U with calf band 513. Calf shell 512 is rotatably coupled to first connecting member 516 with first calf shell connecting member fastener 518. Heel shell 514 is rotatably coupled to first connecting member 516 with first heel shell connecting member fastener 520. Heel shell 514 is further mechanically coupled to foot strap 522 with first foot strap fastener 524.

Calf shell 512 is operably connected to calf shell flap 526 with calf shell flap connector 527. Calf shell flap 526 is operable connected to calf shell ring 528. Heel shell 514 is operably connected to heel shell flap 530 with heel shell flap connector 532. Heel shell flap 530 is operable connected to heel shell ring 534.

Cord assembly 540 further comprises flat cord 548. Flat cord 548 is wrapped around to calf shell ring 528 and attached to itself with first end clip 546. Flat cord 548 is wrapped around heel shell ring 534 and attached to itself with second end clip 549. As noted above, there can be folds, cloth and rings that assist in the connection as well such as sheath 544 or 44

Turning to FIG. 12, one embodiment of the movement limiting system 610 comprises calf shell 612 connected to heel shell 614. Calf shell 612 can be connected to a calf of user U with calf band 613. Calf shell 612 is rotatably coupled to first connecting member 616 with first calf shell connecting member fastener 618. Heel shell 614 is rotatably coupled to first connecting member 616 with first heel shell connecting member fastener 620. Heel shell 614 is further mechanically coupled to foot strap 622 with first foot strap fastener 624.

Calf shell 612 is operably connected to calf shell flap 626 with calf shell flap connector 627. Calf shell flap 626 is operable connected to calf shell ring 628. Heel shell 614 is operably connected to heel shell flap 630 with heel shell flap connector 632. Heel shell flap 630 is operable connected to heel shell ring 634.

Cord assembly 640 further comprises flat cut cord 648. Flat cut cord 648 is wrapped around to calf shell ring 628, heel shell ring 634 and attached to itself with second end clip 649. As noted above, there can be folds, cloth and rings that assist in the connection as well such as sheath 644. As noted above any double cord embodiment can be a single loop or cut with an assembly clip. When a solid loop is used the ring is split and opened to connect the cord and fused back into original shape.

Figure 13:
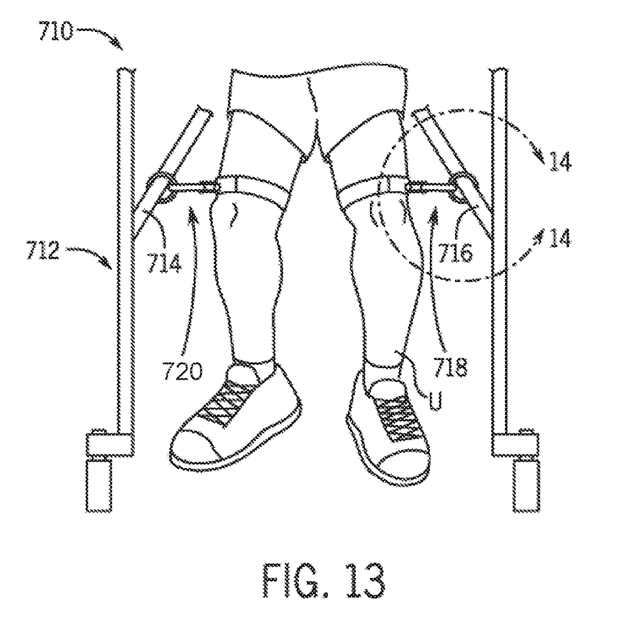
FIG. 13 is a front perspective view of an embodiment of the invention.
Figure 14:
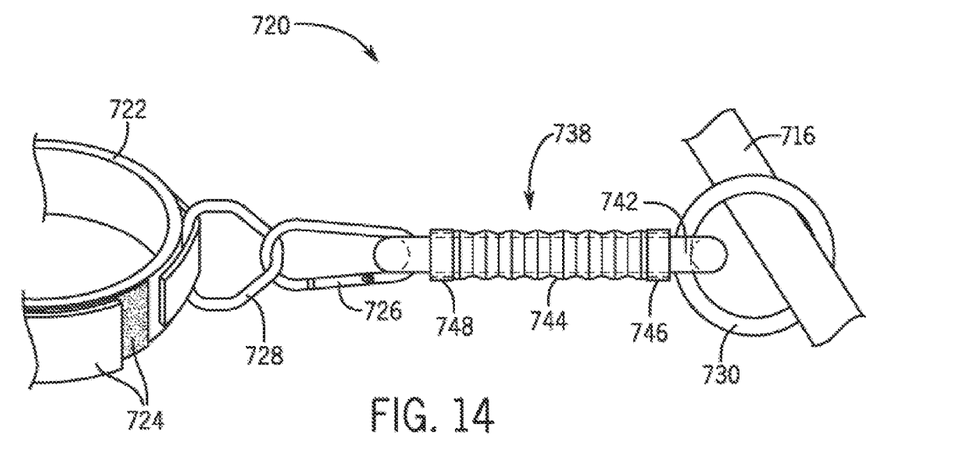
FIG. 14 is a detail perspective view indicated by line 14-14 of FIG. 13.

Turning to FIGS. 13 and 14, one embodiment of movement limiting system 710 comprises walker 712. Walker 712 further comprises first structural member 714 connected to a first wheel and second structural member 716 connected to a second wheel. First structural member 714 is connected to a first leg on user U with first structural member connection assembly 718. Second structural member 716 is connected to a second leg on user U with second structural member connection assembly 720.

Second structural member connection assembly 720 further comprises cuff 722 configured to be wrapped around a thigh of user U and attached to user U with hook and loop fastener 724. Cuff 722 is operatively coupled to carabiner 726 with first ring 728. Carabiner 726 is connected to second ring 730 with dynamic cord assembly 738. Dynamic cord assembly 738 further comprises cord 742. Cord 742 is covered by sheath 744 such that sheath 744 is longer than cord 742. A first end of cord 742 and sheath 744 are then slid over and around second ring 730 and sealed around second ring 730 with first end clip 746. Following that, second end of cord 742 and sheath 744 are then slid over and around carabiner 726 and sealed around carabiner 726 with second end clip 748.

As used in this application, the term "a" or "an" means "at least one" or "one or more."

As used in this application, the term "about" or "approximately" refers to a range of values within plus or minus 10% of the specified number.

As used in this application, the term "substantially" means that the actual value is within about 10% of the actual desired value, particularly within about 5% of the actual desired value and especially within about 1% of the actual desired value of any variable, element or limit set forth herein.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Any element in a claim that does not explicitly state "means for" performing a specified function, or "step for" performing a specified function, is not to be interpreted as a "means" or "step" clause as specified in 35 U.S.C. § 112, ¶6. In particular, any use of "step of" in the claims is not intended to invoke the provision of 35 U.S.C. § 112, ¶6.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:
1. A movement limiting system, comprising:
   a calf shell adapted to form around a calf of a user, the calf shell including a first side surface, a second side surface, and a back surface;
   a calf shell flap connected to a top portion of the back surface of the calf shell, the calf shell flap comprising an opening through a portion of the calf shell flap;
   a calf shell ring extending through the opening of the calf shell flap; a heel shell adapted to form around a heel of the user, the heel shell including a first side surface, a second side surface, a bottom surface, and a back surface;
   a heel shell flap connected to a top portion of the back surface of the heel shell, the heel shell flap comprising an opening through a portion of the heel shell flap;
   a heel shell ring extending through the opening of the heel shell flap;
   a cut cord comprising:
      a circular band cut to form a band with a first end and a second end wherein:

a length of the cut cord is greater than a distance between the calf shell ring and the heel shell ring;
the first end of the cut cord extends through the heel shell ring;
an end clip to connect the first end of the cut cord to the second end of the cut cord; and
a sheath covering the cut cord, a length of the sheath being longer than a length of the cord, wherein the sheath wraps around and is sealed to both the calf shell ring and the heel shell ring and covers the cut cord.

2. The movement limiting system of claim 1, wherein the end clip fuses the first end of the cord to the second end of the cut cord.

3. The movement limiting system of claim 2, further comprising a first end sheath and a second end sheath covering a portion of the sheath.

4. The movement limiting system of claim 2, wherein the sheath is defined length that exceeds the length of the fused cord to eliminate tearing of the fused cord.

5. The movement limiting system of claim 2, wherein the end clip is to fuse the sheath to the cut cord.

6. A movement limiting system, comprising:
a calf shell adapted to form around a calf of a user, the calf shell including a first side surface, a second side surface, and a back surface;
a calf shell flap connected to a top portion of the back surface of the calf shell, the calf shell flap comprising an opening through a portion of the calf shell flap;
a calf shell ring extending through the opening of the calf shell flap; a heel shell adapted to form around a heel of the user, the heel shell including a first side surface, a second side surface, a bottom surface, and a back surface;
a heel shell flap connected to a top portion of the back surface of the heel shell, the heel shell flap comprising an opening through a portion of the heel shell flap;
a heel shell ring extending through the opening of the heel shell flap;
a band with a first end and a second end, wherein:
a length of the band is greater than a distance between the calf shell ring and the heel shell ring;
the first end of the band extends through the calf shell ring; and the second end of the band extends through the heel shell ring; a first end clip to connect the first end of the band to a top portion of the band to form a loop around the calf shell ring; and
a second end clip to connect the second end of the band to a bottom portion of the band to form a loop around the heel shell ring; and
a sheath covering the band a length of the sheath being longer than a length of the band, wherein the sheath raps around and is sealed to both the calf shell ring and the heel shell ring and covers the band.

7. The movement limiting system of claim 6, wherein the first end clip fuses the first end of the band to the top portion of the band.

8. The movement limiting system of claim 6, wherein the second end clip fuses the second end of the band to the bottom portion of the band.

9. the movement limiting system of claim 6, wherein a thickness of the band is less than or equal to 5 millimeters.

10. The movement limiting system of claim 6, wherein a thickness of the band is greater than 5 millimeters.

11. The movement limiting system of claim 6, further comprising a first end sheath and a second end sheath covering a portion of the sheath.

12. The movement limiting system of claim 6, wherein the sheath is defined length that exceeds the length of the band to eliminate tearing of the band.

13. The movement limiting system of claim 6, wherein:
the first end clip is configured to fuse a first end of sheath the first end of the band; and the second end clip is configured to fuse a second end of sheath the second end of the band.

14. A Movement limiting system, comprising:
a calf shell adapted to form around a calf of a user;
a calf shell flap connected to a top portion of a back surface of the calf shell;
a calf shell ring extending through an opening of the calf shell flap;
a heel shell adapted to form around a heel of the user; a heel shell flap connected to a top portion of a back surface of the heel shell;
a heel shell ring extending through an opening of the heel shell flap;
a circular band cut to form a band with a first end and a second end, wherein:
a length of the circular band is greater than a distance between the calf shell ring and the heel shell ring;
the first end of the circular band extends through the calf shell ring; and the second end of the circular band extends through the heel shell ring;
an end clip to connect the first end of the circular band to the second end of the circular band; and
a sheath covering the circular band, a length of the sheath being longer than a length of the circular band, wherein the sheath wraps around and is sealed to both the calf shell ring and the heel shell ring and covers the circular band.

15. The movement limiting system of claim 14, wherein the end clip fuses the first end of the circular band to the second end of the circular band.

16. The movement limiting system of claim 14, further comprising a first end sheath and a second end sheath covering a portion of the sheath.

17. The movement limiting system of claim 14, wherein the sheath is defined length that exceeds the length of the circular band to eliminate tearing the circular band.

* * * * *